US00PP22460P2

(12) United States Plant Patent
Hofmann

(10) Patent No.: US PP22,460 P2
(45) Date of Patent: Jan. 17, 2012

(54) *ERYSIMUM* PLANT NAMED 'INNERYRYSISTAR'

(50) Latin Name: *Erysimum hybrida*
Varietal Denomination: Inneryrysistar

(75) Inventor: Silvia Hofmann, Mainz (DE)

(73) Assignee: InnovaPlant GmbH & Co. KG, Gensingen (DE)

( * ) Notice: Subject to any disclaimer, the term of this patent is extended or adjusted under 35 U.S.C. 154(b) by 0 days.

(21) Appl. No.: 12/927,904

(22) Filed: Nov. 29, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell

(74) *Attorney, Agent, or Firm* — Mark P. Bourgeois

(57) ABSTRACT

A new cultivar of *Erysimum* plant named 'Inneryrysistar' that is characterized by large yellow flowers, a long flowering season, profuse flowering and a compact habit.

1 Drawing Sheet

Botanical classification: *Erysimum hybrida.*
Variety denomination: 'Inneryrysistar'.

BACKGROUND OF THE INVENTION

The present invention relates to a new and distinct cultivar of *Erysimum* plant botanically known as *Erysimum hybrida* and hereinafter referred to by the cultivar name 'Inneryrysistar'.

The new *Erysimum* is the product of a planned breeding program conducted by the inventor in Gensingen, Germany. The objective of the breeding program is to create new *Erysimum* cultivars with large flowers, a long flowering season and a compact habit.

'Inneryrysistar' is a hybrid that originated from a crossing in the Spring of 2007 of the female or seed parent *Erysimum* 'Inneryrysigol' (not patented) and the male or pollen parent a proprietary *Erysimum* identified as ER 05-25-10 (not patented). The resulting seeds were subsequently planted and grown. The cultivar 'Inneryrysistar' was selected by the inventor in the Spring of 2008 as a single plant within the progeny of the stated cross in Gensingen, Germany.

Asexual reproduction of the new cultivar 'Inneryrysistar' first occurred by terminal cuttings in the Summer of 2008 in Gensingen, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Erysimum* cultivar 'Inneryrysistar'. These traits in combination distinguish 'Inneryrysistar' as a new and distinct cultivar apart from other existing known varieties of *Erysimum.*

1. *Erysimum* 'Inneryrysistar' exhibits large yellow flowers.
2. *Erysimum* 'Inneryrysistar' exhibits a long flowering season.
3. *Erysimum* 'Inneryrysistar' exhibits profuse flowering.
4. *Erysimum* 'Inneryrysistar' exhibits a compact habit.

The closest comparison cultivar is *Erysimum* 'Inneryrysimoon' (not patented).

'Inneryrysistar' is distinguishable from 'Inneryrysimoon' by the following characteristics:

1. 'Inneryrysistar' has darker yellow flowers than 'Inneryrysimoon'.
2. 'Inneryrysistar' has flowers that fade to light yellow. The flowers of 'Inneryrysimoon' fade to cream-white.

'Inneryrysistar' is distinguishable from the female or seed parent *Erysimum* 'Inneryrysigol' by the following characteristics:

1. 'Inneryrysistar' has larger flowers than 'Inneryrysigol'.
2. 'Inneryrysistar' has flowers that fade to light yellow. The flowers of 'Inneryrysigol' are yellow and do not fade.
3. 'Inneryrysistar' has a larger quantity of flowers than 'Inneryrysigol'.
4. 'Inneryrysistar' has leaves that are more undulating than 'Inneryrysigol'.
5. 'Inneryrysistar' has a longer flowering season than 'Inneryrysigol'.

'Inneryrysistar' is distinguishable from the male or pollen parent *Erysimum* identified as ER 05-25-10 by the following characteristics:

1. 'Inneryrysistar' has darker yellow flowers than ER 05-25-10.
2. 'Inneryrysistar' has a more compact habit than ER 05-25-10.
3. 'Inneryrysistar' has a more vigorous growing habit than ER 05-25-10.
4. 'Inneryrysistar' has a longer flowering season than ER 05-25-10.

BRIEF DESCRIPTION OF THE DRAWING

The accompanying photograph illustrates the distinguishing traits of *Erysimum* 'Inneryrysistar'. The plant in the photograph shows an overall view of a 6 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Erysimum* cultivar named 'Inneryrysistar'. Data was collected in Gensingen, Germany from 6 month old glass greenhouse grown plants in 13 cm. diameter containers. The time of year was Winter and the temperature range was 5-10 degrees Centigrade during the day and 3-5 degrees Centigrade at night. The light level was 3000 lux. No photoperiodic treatments were used. Color determinations are in accordance with The Royal Horticultural Society Colour Chart 2007 edition, except where general color terms of ordinary dictionary significance are used. The growing requirements are similar to the species. 'Inneryrysistar' has not been tested under all possible conditions and phenotypic differences may be observed with variations in environmental, climatic, and cultural conditions, however, without any variance in genotype.

Botanical classification: *Erysimum hybrida* 'Inneryrysistar'.

Annual or perennial: Perennial.

Parentage: 'Inneryrysistar' is the product of the female or seed parent *Erysimum* 'Inneryrysigol' and the male or pollen parent *Erysimum* ER 05-25-10.

Vigor: Strong.

Growth habit: Upright, bushy.

Plant shape: Rounded.

Suitable container size: 13 to 16 cm. pots.

Height: 20 cm. in height.

Width: 20 cm. in width.

Low temperature tolerance: −6° Centigrade.

High temperature tolerance: 30° Centigrade.

Propagation: Terminal cuttings.

Time to initiate roots in summer: 14 to 18 days to initiate roots at 18 to 20° Centigrade.

Time to initiate roots in winter: 18 to 25 days to initiate roots at 16° Centigrade.

Time to produce a rooted cutting or liner in summer: 20 to 24 days at 18 to 20° Centigrade.

Time to produce a rooted cutting or liner in winter: 25 to 30 days at 16° Centigrade.

Crop time: Approximately 6 months.

Root system: Fine and fibrous.

Stem:

- *Basal branching.*—Yes.
- *Average number of lateral branches.*—5.
- *Pinching.*—Yes.
- *Lateral branch diameter.*—4 mm. in diameter.
- *Lateral branch length.*—20 cm. in length.
- *Internode length.*—5 mm.
- *Stem appearance.*—Striated.
- *Stem aspect.*—Upright.
- *Stem strength.*—Strong.
- *Stem color.*—138B.
- *Pubescence.*—Strong.

Foliage:

- *Leaf arrangement.*—Alternate.
- *Compound or single.*—Single.
- *Number of leaves per lateral branch.*—120.
- *Leaf shape.*—Lanceolate.
- *Leaf apex.*—Acuminate.
- *Leaf base.*—Attenuate.
- *Leaf length.*—9 to 10 cm. in length.
- *Leaf width.*—1.5 cm. in width.
- *Texture.*—Glabrous both sides.
- *Pubescence.*—Short hairs on both sides.
- *Leaf margin.*—Entire, undulate.
- *Venation pattern.*—Pinnate.
- *Young leaf color* (*upper surface*).—137A.
- *Young leaf color* (*lower surface*).—138B.
- *Mature leaf color* (*upper surface*).—137A.
- *Mature leaf color* (*lower surface*).—138B.
- *Vein color* (*upper surface*).—144B.
- *Vein color* (*under surface*).—144B.
- *Leaf attachment.*—Petiolate.
- *Petiole dimensions.*—2.0 cm. in length and 2 mm. in diameter.
- *Petiole color.*—144B.
- *Durability of foliage to stress.*—Strong.

Flower:

- *Inflorescence arrangement.*—Single flowers on terminal racemes.
- *Inflorescence dimensions.*—10 cm. in height and 5 cm. in width.
- *Quantity of flowers per inflorescence.*—8 to 10.
- *Quantity of flowers per lateral stem.*—8 to 10.
- *Quantity of flower buds per lateral stem.*—12.
- *Quantity of flowers and buds per plant.*—Average 400.
- *Natural flowering season.*—Late winter to early summer.
- *Time to flower.*—6 months.
- *Rate of flower opening.*—Every 4 to 5 days.
- *Fragrance.*—Light, vanilla honey.
- *Flower bud length.*—15 mm.
- *Flower bud diameter.*—5 mm.
- *Flower bud shape.*—Ovate.
- *Bud color.*—144A.
- *Rate of bud opening.*—4 to 5 days.
- *Flower aspect.*—Outward.
- *Flower shape.*—Cruciform.
- *Flower dimensions.*—3 cm. in diameter and 2 mm. in height.
- *Flower longevity.*—4-5 days.
- *Number of petals.*—4.
- *Fused or unfused.*—Unfused.
- *Petal shape.*—Ovate.
- *Petal margin.*—Entire, undulate.
- *Petal apex.*—Rounded.
- *Petal base.*—Acuminate.
- *Petal length.*—1.5 cm.
- *Petal width.*—1.8 cm.
- *Petal color when opening* (*upper side*).—9A.
- *Petal color when opening* (*under side*).—9A.
- *Petal color fully opened* (*upper side*).—5B.
- *Petal color fully opened* (*under side*).—5B.
- *Petal color fading to.*—5D.
- *Self-cleaning or persistent.*—Self-cleaning.

Sepals:

- *Sepal appearance.*—Fused.
- *Number of sepals.*—4.
- *Sepal shape.*—Lanceolate.
- *Sepal margin.*—Entire.
- *Sepal apex.*—Acuminate.
- *Sepal base.*—Obtuse.
- *Sepal dimensions.*—15 mm. in length and 3 mm. in width.
- *Young sepal color* (*upper side*).—144A.
- *Young sepal color* (*under side*).—144A.
- *Mature sepal color* (*upper side*).—2A.
- *Mature sepal color* (*under side*).—2A.

Calyx:

- *Calyx shape.*—Lyriform.
- *Calyx dimensions.*—12 mm. in length and 8 mm. in diameter.

Peduncle:

*Peduncle dimensions.*—10 mm in length and 4 mm. in diameter.

*Peduncle angle.*—90 degrees from vertical.

*Peduncle strength.*—Strong.

*Peduncle color.*—137D.

Pedicels:

*Pedicel dimensions.*—10 mm. in length and 4 mm. in diameter.

*Pedicel angle.*—40 degrees from peduncle.

*Pedicel strength.*—Medium.

*Pedicel color.*—137D.

Reproduction organs:

*Stamen.*—Absent.

*Pistil number.*—1.

*Pistil length.*—10 mm.

*Stigma shape.*—Reniform.

*Stigma color.*—3D.

*Style length.*—2 mm.

*Style color.*—3D.

*Ovary color.*—138C.

Fruit and seed production: Fruit and seed production has not been observed.

Disease and pest resistance: Disease and pest resistance has not been observed.

The invention claimed is:

1. A new and distinct variety of *Erysimum* plant named 'Inneryrysistar' as described and illustrated.

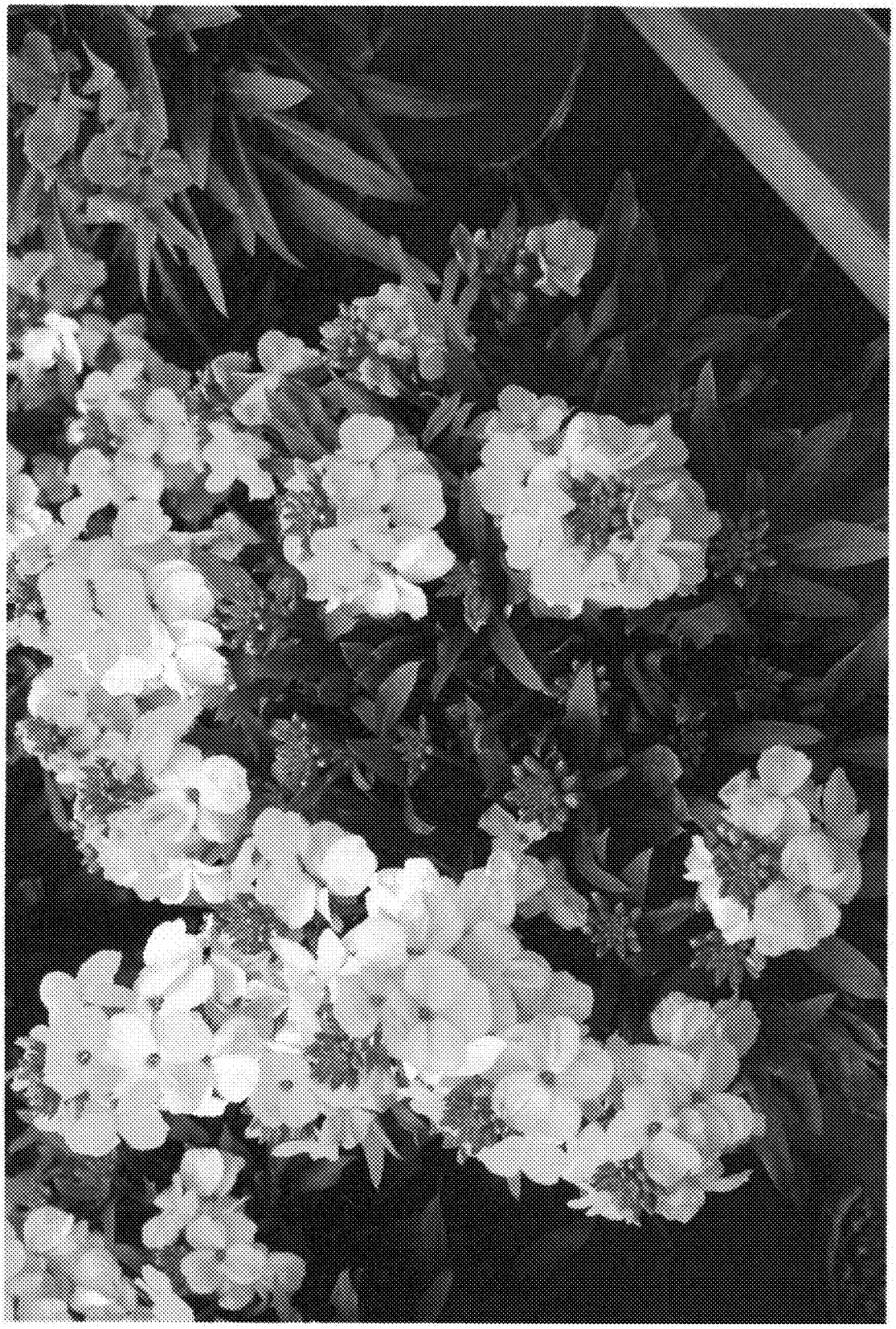

* * * * *